United States Patent [19]

Kaiser et al.

[11] 4,216,783
[45] Aug. 12, 1980

[54] PNEUMATIC MONITOR FOR INDICATING STRENGTH OF CONTRACTILE MUSCLES

[76] Inventors: Howard Kaiser, 1118 Ave. Y, Brooklyn, N.Y. 11235; Laurie A. C. Kaiser, c/o Yondale 248/1 Chemin des Romains, 06250 Mougins, France

[21] Appl. No.: 884,819

[22] Filed: Mar. 9, 1978

[51] Int. Cl.$^2$ .............................................. A61B 5/10
[52] U.S. Cl. .................................... 128/778; 128/748; 73/380; 73/731
[58] Field of Search .............. 116/114 PV; 33/14 BC, 33/174 D; 32/21; 73/379, 380, 146.8, 731; 128/25, 344, 778, 748, 782

[56] References Cited

U.S. PATENT DOCUMENTS

| | | | |
|---|---|---|---|
| 1,354,017 | 9/1920 | Bowden | 73/731 |
| 1,422,256 | 7/1922 | Conrad et al. | 73/146.8 |
| 2,507,858 | 5/1950 | Kegel | 128/25 |
| 4,048,985 | 9/1977 | Sasse | 128/25 |

OTHER PUBLICATIONS

Ciba Clinical Symposia, vol. 4, No. 2, "Stress Incontinence and Genital Relaxation", Arnold H. Kegel, M.D., F.A.C.S. and Orthostatic Incontinence of Urine, S. G. Berkow, M.D., Summit, New Jersey, Feb.-Mar., 1952, pp. 35-61.

Primary Examiner—Robert W. Michell
Assistant Examiner—J. Kruter
Attorney, Agent, or Firm—Cushman, Darby & Cushman

[57] ABSTRACT

This invention relates to a muscle monitor device for providing a visual indication of the strength of contractile muscles, especially the vaginal muscles.

The device is useful both as a preventive and therapeutic biofeedback component for aiding the user to increase the degree and strength of control exercised over the muscles being monitored.

15 Claims, 5 Drawing Figures

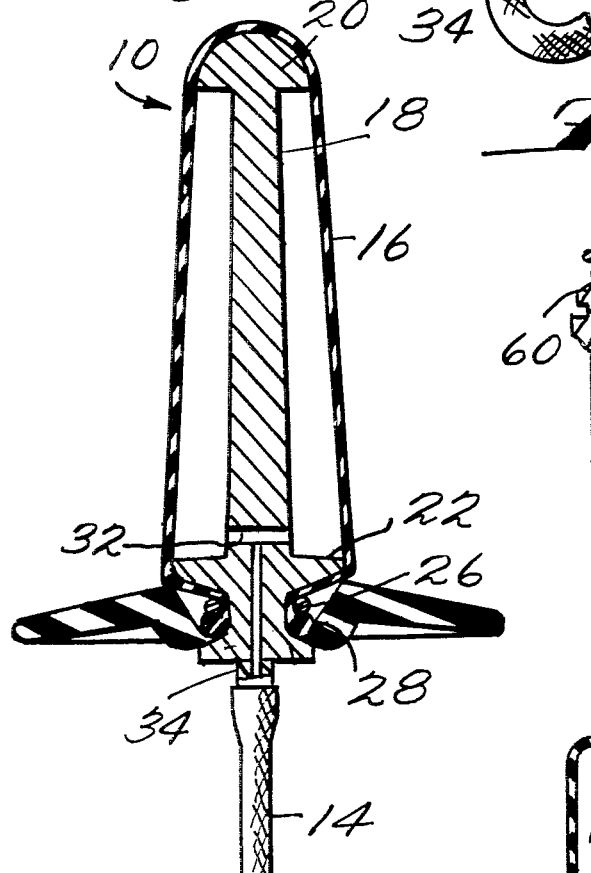
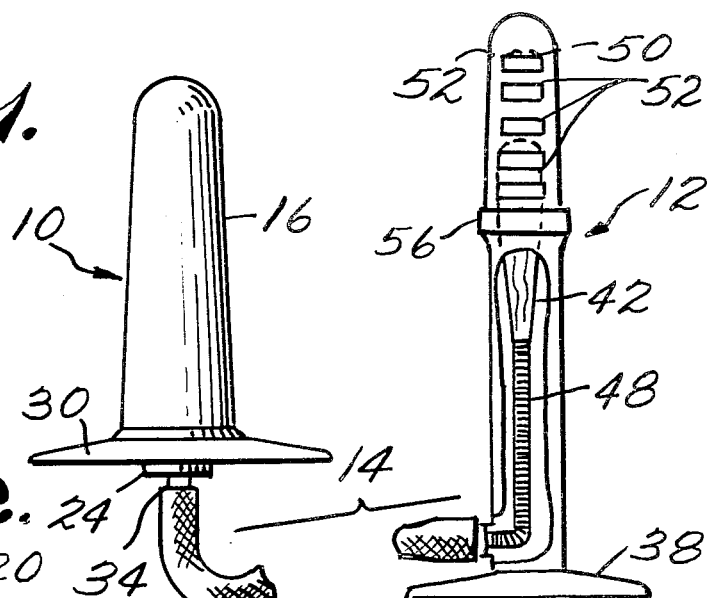
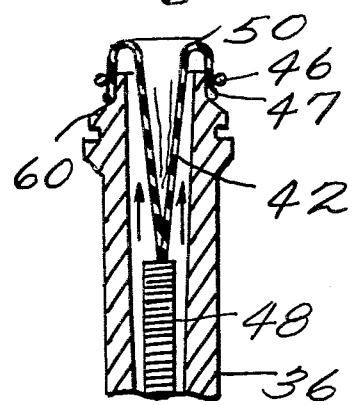
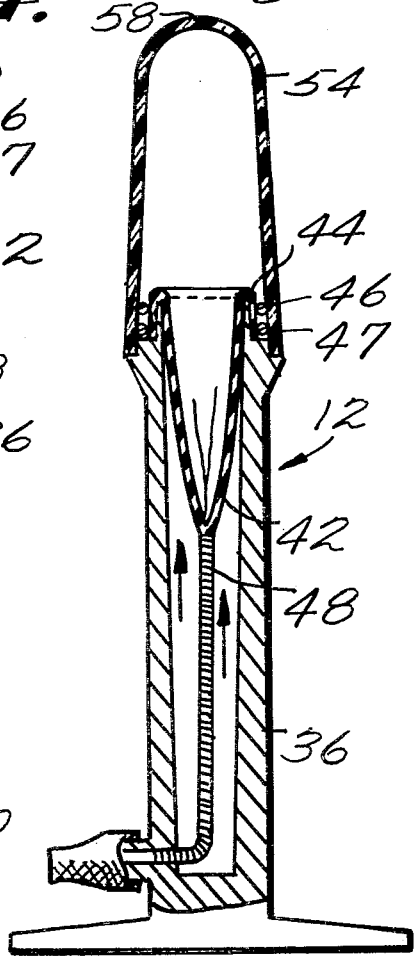
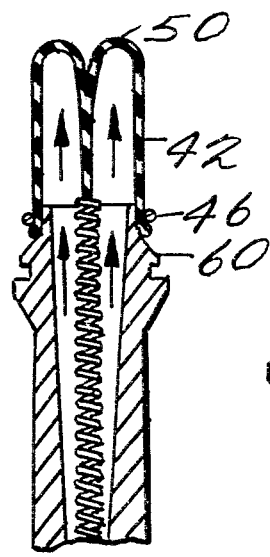

PNEUMATIC MONITOR FOR INDICATING STRENGTH OF CONTRACTILE MUSCLES

BACKGROUND

U.S. Pat. Nos. to Kegel 2,507,858 and 2,541,520 disclose a device for visually indicating contraction of sphincter muscles. The device includes a flexible compressible bulb element insertable into the sphincter muscle and a hand-held, dial-and-pointer type of pressure gauge connected to the bulb by a flexible tube. Upon contraction of the muscle around the compressible bulb, the air pressure in the bulb and the tube rises and is indicated by the pointer on the dial. The device is intended primarily to aid the user in learning to exercise and thereby strengthen or regenerate a weak muscle which may have been injured or otherwise rendered incapable of properly performing its normal physiological function. By observing the degree of movement of the pointer, the user is better able to gain control of the muscle and to progressively increase its strength and endurance over a period of time by regular exercise against resistance, thereby improving its tone and function.

The Kegel monitor has also been employed to measure the strength of contraction of the vaginal muscles, particularly the pubococcygeus whose function is both supportive and sphincteric in action. Ciba Clinical Symposia, Vol. 4, No. 2, February-March 1952, pages 35-51, describes the use of the monitor to assist women in learning to strengthen their vaginal muscles to overcome various lower pelvic musculature problems including some types of urinary stress incontinence and genital relaxation during child bearing and early menopausal years. The publication also reports studies showing that dysfunction of the pubococcygeus exists in many women who suffer a lack of vaginal feeling during intercourse and that in many of these cases sexual appreciation can be restored or increased by restoring the function of the pubococcygeus. The age of the woman in physiological therapy has little or no significance so long as she is mentally alert and capable of intelligent cooperation.

Another important application for the monitor is prophylatic. Exercise in the pre-partum and post-partum periods and also before and after plastic operations involving the sphincteric and supportive structure of the pelvic outlet are specific indications for its use.

SUMMARY OF THE INVENTION

The present invention is directed to an improved muscle monitor of the general type, summarized above, which converts air pressure changes resulting from compression and relaxation of a flexible bulb element to visual indications of muscle movement. The monitor operation has a dual purpose. First, it is intended primarily for monitoring vaginal muscles and is therefore highly sensitive to muscle contractions. Second, it has a variable resistance type of capability that is effective to develop muscle strength and endurance during exercise. The gauge portion of the device converts the slight changes in the internal air pressure of the desire during muscle contraction or relaxation to vertical movement of an indicator assembly, without assistance of the mechanical parts, by means of a mechanically simple, essentially maintenance-free, low-cost mechanism which does not include any complex, easily-broken components. Further the gauge portion of the device is in the form of a stand which can be supported on a table-top or the like within view of the user. Moreover, the indicator assembly is highly visible and due to its special construction is easier to interpret than a dial-and-pointer instrument.

The movable portion of the gauge or indicator assembly includes a finger-shaped balloon or diaphragm constructed of thin elastomeric material such as latex. The balloon element has an open end connected to one end of a rigid barrel which is in communication with the flexible tube leading from the compressible bulb. The barrel is attached to, or integral with, a base which rests on a table top or the like so as to maintain the barrel in a desired position, preferably vertical. The closed end of the balloon is secured to one end of a spiral tension spring disposed within the barrel. When the air pressure in the barrel is equal to atmospheric pressure, the balloon is in a relaxed state and spring retracts the balloon into the barrel.

Upon an increase in air pressure in the barrel, the balloon begins to reverse itself against the action of the spring, with the result that a circumferential portion on the balloon protrudes slightly from the end of the barrel. As the internal air pressure continues to increase, the degree of protrusion increases so that the length of the balloon residing outside the barrel is directly proportional to the internal air pressure which in turn is directly proportioned to the amount of compression of the bulb. A removable transparent cap extending from the end of the barrel receives the protruding balloon to guide the latter and to protect it from damage. Circumferential scale marks on the cap allow the user to note and record the extent of balloon protrusion during a progressive series of exercises.

In a preferred embodiment, the barrel is transparent so that the spring is visible to the user. The spring can be made from a rather long spiral of brightly colored plastics material so that even a slight extension of the spring produces a noticeable movement of the coils away from one another.

DETAILED DESCRIPTION

In the drawings:

FIG. 1 is an elevational view of a muscle monitor embodying the principles of the present invention;

FIG. 2 is a longitudinal sectional view, on an enlarged scape relative to FIG. 1, of the bulb portion of the monitor;

FIG. 3 is a longitudinal sectional view, on an enlarged scale relative to FIG. 1, of the gauge portion of the monitor; and FIGS. 4 and 5 are fragmentary sectional views illustrating the operation of the gauge portion of the monitor.

With reference to FIGS. 1, 2 and 3, it will be seen that the muscle monitor comprises a compressible bulb assembly 10 insertable into the vagina, a gauge assembly 12 for visually indicating air pressure changes generated by the bulb assembly 10 in use and a flexible tube 14 connecting the two assemblies 10 and 12.

The bulb assembly 10 comprises a soft flexible elastomeric sheath 16 fitted over a central rigid post 18 of plastics material or metal. The post 18 has a hemispherical outer end 20 of enlarged cross section relative to the body of the post and at its inner end are two radial shoulders of flanges 22 and 24. The sheath 16, which has a closed outer end, is lightly stretched over the outer end 20 of the post 18 and is sealed to the inner end of the post 18 by an elastic O-ring 26. An integral reinforcing bead 28 on the mouth of the sheath 16 prevents the sheath 18 from tearing as it is stretched over the flange 22. A soft rubber circular flange 30 having a central hole therein is releasably attached to the inner end of the post 18 by pressing the flange 30 into the space between the flanges 22 and 24. An air passage 32 extends from the space between the post 18 and the sheath 16 through the core of the post 18 to a connection 34 over which the flexible air tube 14 is forced.

The gauge assembly 12 includes a vertical barrel 36 which is fitted at its lower end with a base 38 to enable the barrel to be supported in an upright position on a table top or other flat surface. Preferably, the barrel and base are formed integrally from plastics material and preferably the material is transparent. A lateral fitting 40 at the lower end of the barrel 36 is frictionally engaged with the flexible air tube 14 so that the interior of the barrel 36 is in communication with the interior of the bulb assembly 10.

The open upper end of the barrel 36 connects with the interior of an elongated finger-shaped inflatable balloon 42 or diaphram constructed of thin flexible elastomeric material. As seen in FIGS. 3, 4 and 5, the balloon 42 is attached to the barrel 36 by forcing its mouth end over a circumferential lip 44 on the barrel 36 and securing it with an elastic O-ring 46. A bead 47 on the balloon mouth prevents tearing of the balloon 42. The opposite end of the balloon 42 which is closed, is attached to one end of a spiral tension spring 48, the other end of which is fixed in position by being frictionally engaged within the bore of the lateral fitting 40. Thus, in its relaxed, uninflated condition, the balloon 42 is wholly recessed into the barrel 36 by the action of the spring 48, as seen in FIGS. 1 and 3.

An increase in the air pressure in the barrel resulting from compression of the bulb assembly 10 progressively forces the balloon 42 out of the barrel 36 as shown in FIGS. 4 and 5 and in dotted lines in FIG. 1. More specifically, as seen in FIGS. 4 and 5, as the air pressure in the barrel 36 increases, the balloon 42 tends to reverse itself, with the result that an annular portion 50 of the balloon 42 begins to project above the end of the barrel 36. As the air pressure continues to increase, the annular balloon portion 50 continues to rise until the balloon 42 is fully inflated, at which point the annular portion has disappeared. Any further increase in air pressure would first tend to expand the balloon 42 radially and then longitudinally in the channel. The spring 48 is, of course, stretched by inflation of the balloon 42 with the result that the individual coils become progressively further spaced apart, as seen in FIGS. 3, 4 and 5. Thus pressure changes in the barrel 42 are visually indicated by projection and retraction of the balloon 42 and by movement of the coils of the spring 48. It has been found that slight movement of the upper coils is visible to an observer before any projection of the balloon 42 is noticed, and this feature renders the gauge highly sensitive to very slight compression or relaxation of the bulb assembly 10. In addition, even when the balloon 42 is in a protruded position, very slight pressure changes which are insufficient to produce any significant movement of the balloon 42 will produce noticeable movement of the spring coils.

An elongated cap 52, made of transparent plastics material or provided with a window, is detachably connected over the upper end of the barrel 36. The cap 52 surrounds the balloon 42 when the latter is in an inflated, protruding position and is provided with scale marks 54 which indicate to an observer the degree of balloon protrusion. The lower end portion of the cap surrounds the upper end portion of the barrel 36 and is made opaque as by knurl marks 56 so as to obscure the bead 47 on the balloon 42. A small vent hole 58 is provided in the outer end of the cap 52.

The detachable connection between the cap 52 and the barrel 36 may be of any conventional form. As shown, the connection is a snap-on connection formed by an annular rib 60 on the barrel 36 and by a cooperating annular groove (not shown) inside the cap 52.

The spring 48 and balloon 42 are made of brilliantly colored material to improve the visibility thereof. The spring 48 can be made of plastics material. Preferably, the diameter of the coils is relatively large so that movement of the coils toward and away from each other is readily apparent to an observer.

To use the monitor, the bulb assembly 10 is inserted into the vagina to the extent permitted by the soft rubber flange 30. Upon contraction of the vaginal muscles, the flexible sheath 16 of the bulb assembly 10 is compressed slightly radially inwardly, thereby increasing the air pressure in the space between the sheath and the post 18. Air flows through the passage 32 and the tube 14 into the barrel 36 of the gauge assembly 12. As described above, this pressurizing of the interior of the barrel 36 forces the balloon 42 to move from its relaxed recessed position (FIGS. 1 and 3) to a protruded position above the upper end of the barrel 32 and within the cap 52, the extent of protrusion being proportional to the radial compression of the bulb assembly 10. Upon relaxation of the vaginal muscles, the sheath and balloon being elastomeric return to their FIG. 3 contours. Very weak vaginal contraction may effect essentially no noticeable movement of the balloon 42 but the spring 48, especially the uppermost coils, will begin to move before motion of the balloon 42 is observable. As the spring 48 is brilliantly colored, even slight movement of its coils toward or away from each other is easily detectable.

Thus the gauge is highly sensitive to very slight muscular contraction. Stronger contractions result in more positive protrusion of the balloon and these can be read by the user in terms of the scale marks 54 on the cap 52.

What is claimed is:

1. In a monitor for indicating movement of contractile muscles in the wall of a body cavity including a compressible bulb assembly insertable into the body cavity and a gauge assembly connected to the bulb assembly and responsive to air pressure changes effected in the assemblies by contraction and relaxation of the muscles in the wall of the body cavity, an improved gauge assembly which comprises a barrel having an interior chamber in communication with the interior of the bulb assembly, a balloon having inner and outer surfaces and a mouth connected to the barrel to expose one of said surfaces of the balloon to the air pressure in the barrel chamber, the wall of said balloon being movable into and out of one end of said barrel, means biasing said balloon to a position within said chamber such that upon a predetermined increase in air pressure in said chamber said biasing means is overcome and said balloon begins to move out of said one end of said barrel to thereby indicate the degree of contraction of the contractile muscle.

2. A monitor as in claim 1 wherein said biasing means is a spiral tension spring located in said barrel and attached at one end to the wall of said balloon and its other end being fixed with respect to said barrel.

3. A monitor as in claim 2 wherein said barrel is vertically elongated and includes a base of enlarged lateral dimension for supporting said barrel in an upright position on a horizontal support surface, the mouth of said balloon being connected to the upper end of said barrel.

4. A monitor as in claim 3 including an elongated cap detachably connected to the upper end of said barrel to receive said balloon when the latter is moved out of the barrel by increased air pressure in said barrel, said cap having scale marks thereon to indicate the amount of protrusion of said balloon from said barrel.

5. A monitor as in claim 4 wherein said cap is transparent.

6. A monitor as in claim 1 wherein the mouth of said balloon is connected to said one end of said barrel, and wherein said biasing means is a tension device located in said barrel and normally biasing said balloon is an inverted condition within said barrel.

7. A monitor as in claim 1 wherein said means which biases said balloon to a position within said chamber is a spiral spring made of plastics material.

8. A gauge for indicating changes in fluid pressure comprising a barrel having an interior chamber; means for connecting the chamber with a source of variable fluid pressure, the changes in which are to be indicated by said gauge; a flexible disphragm extending across an aperture in said barrel and sealed to said barrel, so that one surface of said diaphragm is exposed to the pressure in said chamber, said diaphragm having an area substantially larger than the area of said aperture; yieldable tensioning means attached between said one surface of said diaphragm and the interior of said barrel chamber so as to retract said diaphragm into said chamber when the fluid pressure is below a predetermined value, said tensioning means being sufficiently yieldable at pressures above said predetermined value to allow said diaphragm to be forced through said aperture, the magnitude of the protrusion of said diaphragm being an indication of the fluid pressure in said chamber.

9. A gauge as in claim 8 wherein said diaphragm is an elongated balloon having a mouth connected to said barrel and a closed end opposite said mouth and extendable through said aperture.

10. A gauge as in claim 9 wherein said balloon is in an inverted condition within said barrel when retracted by said yieldable tensioning means.

11. A gauge as in claim 8 wherein said yieldable tensioning means is a spiral spring made of plastics material.

12. In a monitor for indicating movement of contractile muscles in the wall of a body cavity including a compressible bulb assembly insertable into the body cavity and a gauge assembly connected to the bulb assembly and responsive to air pressure changes effected in the assemblies by contraction and relaxation of the muscles in the wall of the body cavity, an improved gauge assembly comprising an elongated barrel having an interior bore, a spiral tension spring extending longitudinally in said bore, one end of the spring being fixed with respect to said barrel and the other end being connected to a flexible balloon having a mouth connected across said bore, said spiral tension spring normally biasing said balloon in a position within said bore, said balloon upon a predetermined increase in air pressure in said bore expanding against the biasing force of said spring so as to stretch said spring and so as to project out of one end of said bore, said spring having coils which move away from each other to an observable degree when said spring is stretched, and said coils being visible through the wall of said barrel.

13. A monitor as in claim 12 wherein said spiral tension spring is made of plastics material.

14. In a monitor for indicating movement of contractile muscles in the wall of a body cavity including a compressible bulb assembly insertable into the body cavity and a gauge assembly connected to the bulb assembly and responsive to air pressure changes effected in the assemblies by contraction and relaxation of the muscles in the wall of the body cavity, an improved gauge assembly comprising: a vertically elongated barrel having an interior bore and being made of transparent material and provided at its lower end with a base of enlarged transverse dimension to enable said barrel to be supported in an upright position on a horizontal support surface; a spiral tension spring extending longitudinally in said bore, one end of the spring being fixed with respect to said barrel and the other end being connected to a flexible diaphragm which is movable in a direction to stretch said spring upon a predetermined increase in the air pressure in said bore, said spring having coils which move away from each other to an observable degree when said spring is stretched, and said coils being visible through the wall of said barrel; and a transparent elongated cap detachably connected to the upper end of said barrel for receiving the projecting portion of said diaphragm.

15. A monitor as in claim 14 wherein said spiral tension spring is made of plastics material.

* * * * *